United States Patent [19]

Polaschegg

[11] Patent Number: 4,894,164
[45] Date of Patent: Jan. 16, 1990

[54] APPARATUS FOR TREATING BLOOD IN AN EXTRACORPOREAL CIRCUIT

[75] Inventor: Hans-Dietrich Polaschegg, Oberursel, Fed. Rep. of Germany

[73] Assignee: Fresenius AG, Bad Homburg von der Hohe, Fed. Rep. of Germany

[21] Appl. No.: 114,346

[22] Filed: Oct. 27, 1987

[30] Foreign Application Priority Data

Oct. 30, 1986 [DE] Fed. Rep. of Germany ....... 3636995

[51] Int. Cl.$^4$ ............................................. B01D 13/00
[52] U.S. Cl. ..................................... 210/646; 210/85; 210/97; 210/149; 210/181; 210/321.65; 210/321.72; 210/650; 210/742; 422/46; 604/5
[58] Field of Search .................. 604/4, 5; 422/46, 48; 210/644, 645, 646, 647, 649, 651, 652, 742, 805, 175, 177, 181, 195.1, 195.2, 321.65, 321.72, 184, 186, 85, 97, 650, 149

[56] References Cited

U.S. PATENT DOCUMENTS 4,370,983 2/1983 Lichtenstein .................... 210/321.65
4,401,431 8/1983 Arp .......................................... 604/4

OTHER PUBLICATIONS

Schaefer et al., "Failure to Show a Temperature-Dependent Vascular Stability During Hemofiltration," *The International Journal of Artificial Organs*, vol. 6, No. 2, 1983, pp. 75-76.
Maggiore et al., "Blood Temperature and Vascular Stability During Hemodialysis and Hemofiltration," *Transactions American* Society Artificial Internal Organs, vol. 28, 1982, pp. 523-527.
Maggiore et al., "Effect of Extracorporeal Blood Cooling on Dialytic Arterial Hypotension," Proceedings EDTA, vol. 18, 1981, pp. 597-602.
Kishimoto et al., "Cardiovascular Stability in Low Temperature Dialysis," *Dialysis and Transplantation*, vol. 15, No. 6, Jun. 1986, pp. 329-333.

Primary Examiner—W. Gary Jones
Attorney, Agent, or Firm—Townsend and Townsend

[57] ABSTRACT

An apparatus for treating blood in an extracorporeal circuit for hemodialysis of hemofiltration and a method for withdrawing heat from blood in an extracorporeal circuit wherein blood is brought into contact along a membrane with a treatment solution which has been heated to a temperature in a source making the treatment of fluid available such that the energy balance of the patient is maintained, the temperature of the source being controlled in that the temperature of the blood emerging from the patient is measured, the temperature value obtained is compared with a predetermined temperature value and on determination of a difference between the two values the source temperature is changed.

22 Claims, 2 Drawing Sheets

APPARATUS FOR TREATING BLOOD IN AN EXTRACORPOREAL CIRCUIT

BACKGROUND OF THE INVENTION

The invention relates to an apparatus for treating blood in an extracorporeal circuit, in particular a hemodialysis apparatus and a hemofiltration apparatus, either of which have an element which is divided by a membrane into two chambers apparatus according to the preamble of claim 1 and a hemofiltration apparatus according to the preamble of claim 2.

A hemodialysis apparatus comprises an exchange element, in particular a dialyzer, which is divided by a membrane into two chambers, the first chamber being connected into a dialysis solution and the second chamber being connected into a blood path, the dialysis solution path comprising a dialysis solution source having at least one concentrate admission, a fresh water source and a temperature control unit and the blood path comprising at least one blood pump and a drip chamber downstream of the dialyzer.

A hemofiltration apparatus comprises a hemofilter which is also divided by a membrane into two chambers, the first chamber serving to receive hemofiltrate, charged with metabolism products, from blood and the second chamber likewise being connected into a blood path. The hemofiltrate amount removed is replaced approximately by an equal amount of substitution solution (minus the amount to be ultrafiltered) which is added to the blood downstream of the exchange element at a predetermined temperature.

The purpose of blood purification apparatuses used in dialysis or hemofiltration is of course to replace non-functioning kidneys in cases of acute or chronic uremia. Although these apparatuses are still not yet perfect it has been possible in the course of time to develop the method so that a large number of chronically uremic patients can survive with satisfactory life quality.

To replace at least the functions necessary for maintaining life, the blood must be freed from uremic toxins, the electrolyte metabolism and the acid-base balance maintained and part of the fluid amount absorbed through foodstuff and beverages removed.

This is mainly done with the method of hemodialysis in which blood in an extracorporeal circuit is led past a semipermeable membrane, past the other side of which a dialysis solution is conducted whose electrolyte composition is substantially equal to that of the blood. When this is done the uremic toxins pass from the blood into the dialysis solution and an equalization of the concentrations results. If a pressure difference is established between the blood and the dialysis solution a passage of fluid will also take place, i.e. of ultrafiltrate, and thus the desired fluid withdrawal. Due to the semipermeable properties of the membrane the vital blood corpuscles and proteins are retained in the blood.

In another known method, that is hemofiltration, blood is conducted in an extracorporeal circuit through a hemofilter by which an ultrafiltrate is withdrawn containing the uremic toxins. At the same time, in a first nutrient an equal quantity of a uremic-toxin-free substitution solution is again added in proportion to the blood. In the exchange element used in this method, which may be a dialyzer or a hemofilter, an exchange thus takes place of fluid components to another fluid or a fluid flows along another fluid, for example blood plasma along dialysis solution. Since these fluids or solutions have different temperatures a temperature or heat exchange also takes place.

In DE-OS 3,313,421 such hemodialysis and hemofiltration apparatuses are described. In these known apparatuses the dialysis solution source or substituate source is heated to a predetermined temperature with a temperature regulating unit, the temperature of the source being passed from a temperature detector to a control unit which controls the heating means in accordance with said measured temperature value and a predetermined temperature value. The predetermined temperature value is entered by the attending physician prior to the dialysis session and thereafter kept constant during the entire treatment.

In an article by Q. Maggiore et al. in Proc. EDTA (1981) Vol. 18, p. 597-602, it is shown that the frequently observed and to this date generally accepted better blood pressure stability in the method of insulated ultrafiltration is due to the fact that in this method thermal energy is withdrawn from the blood of the patient. In particular, it has been found that during conventional hemodialysis as well a better blood pressure stability is achieved if the temperature of the dialysis solution is lowered from the usual value of 37° C. to 34° C. It was however also observed that many patients found this temperature drop unpleasant.

By this step the blood temperature in the arterial tubing system was kept substantially constant. The measuring means used were thermistors inserted directly into the tubing system. Consequently, the entire system had to be subsequently sterilized.

In a later article by Q. Maggiore et al. in Trans Am Soc Artif Intern Organs (1982), Vol. 28, p. 523-527, it is shown that in hemofiltration as well the thermal energy balance influences the circulation stability. Measurements were made from which it is apparent that in conventional hemodialysis energy is supplied to the extracorporeal circuit. This is considered to be a cause for the rise of the body temperature which has a disadvantageous effect on the condition of the patient. As measuring means in the extracorporeal circuit special plastic disposable articles were used which permitted introduction of a thermometer without direct blood contact. A constant measurement deviation of 1° C. occurs.

Whereas K. Schafer et al. in The International Journal of Artificial Organs (1983), Vol. 6, p. 75-76, doubts any influence of the blood temperature and thus the thermal energy balance on the circulation stability, T. Kishimoto et al. in Dialysis & Transplantation (1986) Vol 15., No. 6, p. 329-333, confirmed the opinions of Q. Maggiore in so far as they referred to hemodialysis.

As is known, as a rule a loss of energy occurs on the reflux side in hemodialysis and on the influx and reflux sides in the extracorporeal blood circuit in hemofiltration.

The fixedly entered lowering of the temperature of the dialysis solution is frequently not enough to effect temperature balance. This is due to the reaction of the individual patients to the particular dialysis conditions. Thus, in this respect it is not possible to ensure with the known temperature lowering that the patient is adequately temperature-compensated, i.e. a feverish reaction nevertheless frequently occurs and leads to a reduction of the peripheral resistance of the patient and thus to a considerable strain.

The problem underlying the invention is to further develop the apparatus of the type mentioned at the beginning so that the energy balance of a patient subjected to hemodialysis or hemofiltration is improved.

SUMMARY OF THE INVENTION

According to the invention, therefore, an apparatus is provided for treating blood in an extracorporeal circuit for hemodialysis or hemofiltration fluid and a method is provided for withdrawing heat from blood in an extracorporeal circuit wherein blood is brought into contact along a membrane with a treatment solution which has been heated to a temperature in a source making the treatment of fluid available such that the energy balance of the patient is maintained, the temperature of the source being controlled in that the temperature of the blood emerging from the patient is measured.

According to the invention the blood temperature, which correlates to the body temperature of the patient, is measured and compared with a predetermined value or a number of predetermined values, the temperature of the dialysis solution or the substitution solution being adjusted in accordance with the comparison result.

A second temperature sensor in the venous part of the extracorporeal circuit makes it possible if the blood flow is known, which is usually the case, to determine precisely the heat withdrawal which the patient undergoes without the parameters of the extracorporeal circuit and the dialysis solution temperature or substituate temperature and ambient having to be known exactly.

The arterial blood temperature and/or venous blood temperature measured at the start of the dialysis or the hemofiltration is given as reference temperature. A further reference parameter can result from the difference measured at the start of the dialysis between the arterial and the venous blood temperature. Furthermore, a predetermined performance to be achieved can be set as reference value.

The evaluating and control unit is thus connected on the input side both to the blood pump and to the arterial temperature sensor and also possibly to the venous temperature sensor. On the output side the evaluating and control unit is connected to the temperature regulating unit of the dialysis solution source or of the substituate source.

Via an input device the selected reference values are entered into the evaluating and control unit.

The invention makes it possible by means of measuring the blood temperature in the arterial blood path of the extracorporeal circuit to influence the heat extraction during the hemodialysis operation or also hemofiltration oxygenation in such a manner that the body temperature is kept constant or also varied in definite manner as desired by the physician.

In the tests carried out in vivo, in hemodialysis, dialysis solution temperatures of 37° C. and 34° C. were set and the body temperature and circulation parameters, for example the blood pressure, measured at intervals of several minutes. In addition, in in vivo experiments the heat losses in the extracorporeal circuit were measured in dependence upon the dialysis solution as well as the ambient temperature and the blood flow and it was shown that these three parameters interfer with the heat and temperature balance in the extracorporeal circuit.

Own investigations have shown that with a dialysis solution temperature of 37° C. the blood in the extracorporeal circuit is cooled provided that the room temperature lies in the normal range of 20°-25° C. Nevertheless, the body and blood temperature rise in the arteries. These measurements indicate that the rise of the arterial blood temperature or body temperature depends on the biocompatibility of the hemodialyzer used. The investigations have further shown that apart from the influences mentioned above of the dialysis solution temperature, ambient temperature and blood flow the construction and design of the blood tubing system and hemodialyzer as well as the dialysis solution flow influence the heat balance.

It is apparent from the cited publications that the dialysis solution temperature has an influence on the circulation stability. It is known from own measurements that the rise of the body temperature is not due to warming up of the blood in the extracorporeal circuit. On the contrary, it must be a reaction of the organism to the operation of hemodialysis and it is assumed that the biocompatibility of the materials used has an influence.

These statements apply equally to hemofiltration as well.

The amount of heat to be withdrawn to stabilize the body temperature will therefore depend on the patient-specific parameters, such as sensitivity of the patient, and also on the body weight.

Thus, the amount of heat withdrawn from the patient in the extracorporeal circuit depends on a number of already mentioned parameters. All the other influences mentioned have as a rule not been predicted or at best only approximately.

The invention will be explained in detail with the aid of two examples of embodiment.

DESCRIPTION OF SPECIFIC EMBODIMENTS

Figure 1:
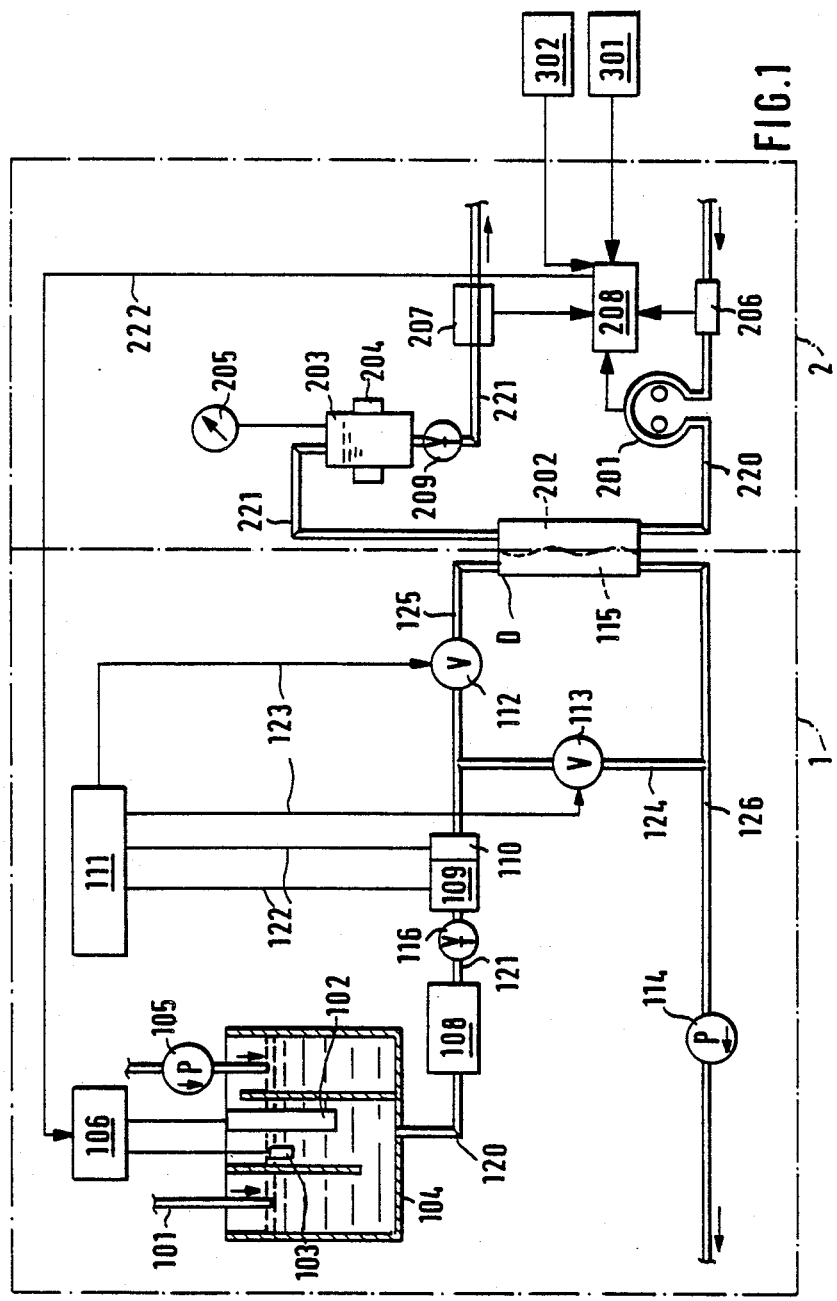
FIG. 1 shows an apparatus for withdrawing heat from blood in the extracorporeal circuit for hemodialysis and FIG. 2 shows a hemofiltration apparatus for the same purpose for hemofiltration.

The hemodialysis apparatus according to FIG. 1 consists of a dialysis solution part 1 and the extracorporeal blood circuit 2. Both parts have a substantially known construction. Thus, a dialysis solution source consists of a water supply 101, the source of which is not shown in detail here, an electrically operated heater 102 with temperature sensor 103 and a pump 105 pumping concentrate as well as a dialysis solution container 104. The electrically operated heater 102 and the temperature sensor 103 are connected to a closed-loop control unit 106 which with the aid of a signal of the temperature sensor 103 controls the heater 102 in such a manner that a predetermined temperature of the dialysis solution is achieved. From the dialysis solution container 104 a conduit 120 leads to a degassing unit 108 known per se. The latter is in turn connected to a conductivity sensor 109 and an associated temperature sensor 110. The signals of said sensors 109 and 110 are processed by a monitoring device 111 and the temperature-compensated conductivity of the dialysis solution calculated therefrom and compared along with the temperature with predetermined alarm limit values and on deviations outside the predetermined alarm window the valves 112 and 113 are controlled so that the dialysis solution is diverted past the dialyzer. A pump 114 disposed downstream of the dialyzer D serves to deliver the dialysis solution and generates in conjunction with a throttle 116 disposed upstream of the dialyzer D a partial vacuum in the dialysis solution compartment 115 of the dialyzer D for the purpose of ultrafiltration.

Figure 2:
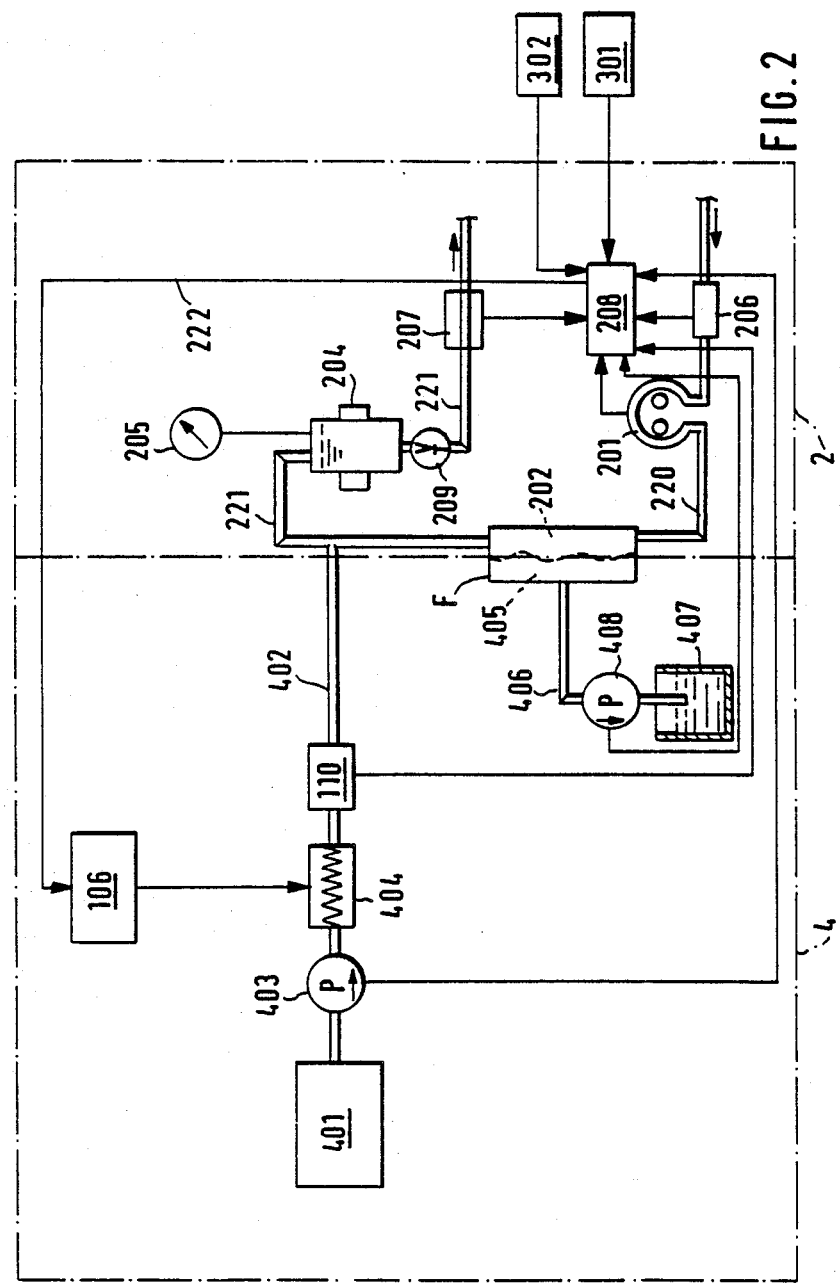

The hemofiltration apparatus according to FIG. 2 has instead of the dialysis solution part 1 a substitution solution part 4 and likewise an extracorporeal circuit 2.

The substitution solution 4 also has a substantially known construction. Thus, it consists of a substitution container 401 followed in a conduit 402 by the substituate pump 403. The latter serves to deliver substitution solution into the tube piece 221 of the venous part of the extracorporeal blood circuit 2. The substituate pump 403 is followed by a heating means 404 which heats the substitution solution to a predetermined temperature value.

For this purpose said heating means 404 is connected to the control unit 106. Between the heating means 404 and the entry of the conduit 402 into the tube piece 221 a second temperature sensor 110 is disposed, the first temperature 206 being inserted upstream into the arterial part 220 of the blood tubing system.

From the filtrate compartment 405 a conduit 406 leads to a collecting container 407 for the hemofiltrate. The hemofiltrate consists of extracted plasma water including the metabolism products and is delivered via the interposed filtrate pump 408 to the collecting container 407. The delivery rate of the filtrate pump 408 is reported to the evaluating and control unit 208 to which the substituate pump 403 and the temperature sensor 110 are also connected for reporting the delivery rate and the temperature o the heated substituate solution respectively.

The extracorporeal circuit 2 is substantially the same in hemodialysis and in hemofiltration and consists upstream of the dialyzer D or the filter F of the blood pump 201, the blood compartment 202 of the dialyzer D or of the filter F, the drip chamber 203 with associated level sensors 204 disposed downstream of the dialyzer D or filter F and a venous pressure monitor 205. Connected into the arterial blood path in the region of the tube piece 220 is a first temperature sensor 206. In the venous blood path in the region of the tube piece 221 leading from the drip chamber 203 back to the patient a further temperature 207 can be disposed. Conventional temperature sensors are used, for example platinum resistors having a nominal resistance of 100 ohm at 0° C. or thermistors, for example NTC or PTC thermistors.

An evaluating and control unit 208 receives the signals of the temperature sensors 206 and 207 and possibly a signal from the blood pump 201 proportional to the blood pump flow. In hemofiltration the evaluating and control unit 208 possibly further receives a signal on the delivery rate of the extracted ultrafiltrate from the filtrate pump 408 and the temperature signal from the temperature sensor 110 as well as from the substituate pump 403. In addition, optional patient-specific or treatment-specific control parameters can be entered with the input device 301. From the control unit 208 a signal line leads to the temperature regulating unit 106 which enables the dialysis solution temperature or the temperature of the substitution solution to be changed.

The temperature sensors 206 and 207 are advantageously so designed that no special disposable articles are necessary. On the other hand, part of the tube piece 220 and 221 is inserted into a housing jointly surrounding the tube piece with the sensor and said housing is so made and insulated that the temperature sensor measures the temperature obtaining at this point in the tubing system to an accuracy of about 0.1° C.

In hemodialysis via the water supply 101 water is introduced into the dialysis solution container. A concentrate is also supplied via the concentrate pump 105. The dialysis solution container 104 serves substantially for heating, degasssing and mixing the dialysis solution, the latter advantageously being carried out volumetrically. With the aid of the electrically operated heater 102 and the associated temperature sensor 103 the water is heated to a previously defined value, for example 34° C.

The pump disposed in the degassing unit 108 and not illustrated in detail inspires the dialysis solution via the conduit 120 and liberates the air dissolved in the dialysis solution. This air is conducted back with a part of the dialysis solution to the mixing chamber of the dialysis solution container 104 from whence it escapes. Details of this have not been shown in the drawings because they are generally known. The degassed dialysis solution is first brought into contact via a conduit 121 with a conductivity sensor 109 and an associated temperature sensor 110. The purpose of the preceding throttle valve 116 is to generate the partial vacuum in the dialysis solution in dependence upon the action of the dialysis solution pump.

The sensors 109 and 110 are connected to a monitoring device 111 by means of the signal line 122 and in the case of a deviation of the dialysis solution from the set values said monitoring device 111 gives an alarm and thereby controls the valves 112 and 113 via the signal line 123. Thus, on deviation of the values set the valve 112 is closed and the valve 113 of the bypass conduit 124 opened, thus preventing dialysis solution of undesired composition or temperature reaching the dialyzer D, the entrance of which is connected to the conduit 125 from the valve 112. The dialysis solution is accordingly delivered via the valve 113 directly to the pump 114.

Downstream of the dialyzer a conduit 126 leads to the pump 114 and is connected downstream to the bypass conduit 124.

In hemofiltration the substituate container 401 is connected to the conduit 402. On starting up the substituate pump 403 the substitution solution is delivered via the conduit 402 to the heating means 404 and there heated to a predetermined temperature value. The temperature sensor 110 measures the temperature of the substitution solution and reports it to the evaluating and control unit 208 whilst the delivery rate of the substituate pump 403 is also reported to the unit 208.

The extracorporeal blood circuit 2 extends via the arterial flexible tube piece 220 and the blood pump 201 to the blood compartment 202 of the dialyzer D or filter F and via the venous tube piece 221, into which the drip chamber 203 is connected, to the patient. The front portion of the tube piece 221 is connected at its one end to the dialyzer D or the filter F and at its other end to the inlet of the drip chamber 203.

The blood is pumped by the blood 201, preferably a hose pump, which delivers the blood corresponding to the desired delivery rate through the extracorporeal circuit 2.

The drip chamber 203 is connected to a level sensor 204 which when the level in the drip chamber 203 drops or on occurrence of air or blood foam gives an alarm, stops the pump 201 and closes the throttle 209 disposed downstream of the drip chamber 203. The venous pressure monitor 205 indicates the venous reflux pressure.

If only one temperature sensor 206 is disposed in the extracorporeal blood circuit the arterial blood temperature thereof is taken as reference temperature for the evaluating and control unit 208. If a temperature sensor 207 is additionally disposed in the venous blood path of the extracorporeal circuit the difference between the arterial temperature sensor 206 and venous temperature sensor 207 can also be selected as reference value for the closed-loop control.

The evaluating and control unit 208 receives the signals of the temperature sensors 206 and 207 and a signal from the blood pump 201 proportional to the blood pump flow. A signal line 222 leads from the evaluating and control unit 208 to the temperature regulating unit 106 permitting adjustment of the temperature setting. The temperature of the dialysis solution or substitution solution is thereby raised or lowered to a temperature value calculated by the evaluating and control unit 208. Thereafter correspondingly temperature-regulated dialysis solution is supplied to the dialyzer D or substitution solution to the venous blood conduit 221. The flowing past of the two media dialysis solution and blood plasma results in an exchange of heat taking place in the dialyzer. This happens in hemofiltration when the substitution solution flows into the blood conduit 221. As a rule an exchange of thermal energy takes place to the blood from the dialysis solution or substitution solution. The body temperature of the patient or his blood temperature is brought to a normal value or a value selected by the physician.

Thereafter the blood thus heated on returning to the patient again loses energy, about 2° C., so that it reaches the patient again in a cooled state and account is taken of this in the determination of the energy balance.

In hemofiltration a blood heat energy value $E_1$ is determined by detection of the temperature value Tl by the temperature sensor 206 and of the delivery volume Vl of the blood pump 201.

$$E_1 = T_1 \times V_1$$

From the temperature loss and the withdrawal of the hemofiltrate an energy value results at the output side of the hemofilter F in the extracorporeal circuit 2 which is given by $$E_2 = T_2 \times (V_1 - V_2),$$

where $T_2$ is known empirically and $V_2$ represents the withdrawn hemofiltrate volume. $T_2$ reaches its value at the point of entry of the substituate conduit 402 into the venous blood conduit 221 of the extracorporeal blood circuit 2. The energy value $E_3$ is derived from the measured temperature value $T_3$ of the temperature sensor 110 and the delivery volume $V_3$ of the substituate pump 403, $$E_3 = T_3 \times V_3$$

The energy value $E_4$ follows from the temperature value $T_4$ and the delivery volume Vl of the blood pump 201 minus the ultrafiltration rate UF, $$E_4 = T_4(V_1 - UF),$$

where $$UF = V_2 - V_3$$

Since the values of $T_1$, $T_2$, $T_4$ and $V_1$, $V_2$, $V_3$ and thus also UF are known or are entered into the evaluating and control unit 208, in said unit an energy balance is conducted as a result of which the temperature value $T_3$ for the supplied substitution solution is determined. The heating means 404 is thereby kept in operation by the regulating unit 106, which receives a corresponding signal from the evaluating and control unit 208, until the temperature of the substitution solution has reached the desired value $T_3$ which has been calculated by the evaluating and control unit 208.

Since the energy value $E_4 = E_2 + E_3$ can be calculated from $$E_4 = T_2(V_1 - V_2) + V_3 \times T_3$$

there is no need to measure the temperature value $T_4$ and consequently the temperature sensor 207 can be omitted.

However, the temperature value of the temperature sensor 207 may also be taken as desired or reference value and entered into the evaluating and control unit 208, said value being compared with the measured value of the temperature sensor 206, said temperature difference giving the temperature actual value of the temperature sensor 110.

Essential to the invention is that the temperature value determined at the extracorporeal blood inlet, i.e. at the temperature sensor 206, is correlated to the temperature value determined at the blood outlet, i.e. at the temperature sensor 207. For the higher the inlet value the lower the outlet value is to be set, i.e. the lower the amount of energy to be supplied extracoporeally to the blood because the body by generation of fever intracorporeally makes available additional energy which must be extracted from the body of the patient extracorporeally. This can be done in hemofiltration in the manner described above in two embodiments, an equalized energy balance being achieved.

The distance from the patient connection to the temperature sensors 206 and 207 is about 1 m. Measurements have shown that with conventional room temperatures between 20° and 25° C. and the usual tubing materials the temperature drop along this distance is about 0.4° C. and this can be compensated by suitable calibration of the evaluating and control unit 208.

The evaluating and control unit 208 can be programmed with the aid of the input unit 301. The following control possibilities are advantageously provided:

1. The value measured by the arterial temperature sensor 206 at the start of the treatment is chosen as reference temperature.

2. The arterial blood temperature to be set by the physician is chosen as reference temperature.

3. The difference between the arterial temperature sensor 206 and venous temperature sensor 207 is chosen as reference for the control.

4. A specific amount of energy to be withdrawn can be preselected.

In an additional display unit designated in the drawing by 302 it is possible to display inter alia:
   the arterial blood temperature;
   the venous blood temperature;
   the amount of energy withdrawn;
   the amount of energy or heat withdrawn since the start of the treatment.

From these, in the display unit the energy balance can be calculated and indicated. In addition, further adjustment possibilities may be provided for setting the control time constants if a suitable adaptive controller on the basis of a microprocessor is not used.

Of course, forms of input other than that shown may be used.

As already mentioned above the display unit 302 can display the arterial blood temperature measured by the sensor 206, the venous blood temperature measured by the sensor 207 and, if the volumes $V_1-V_4$ delivered in the external blood circuit are known, the energy being instantaneously withdrawn from the blood in the exchange element F and on integration over a predetermined interval of time, for example the entire treatment duration, the amount of energy withdrawn.

According to a further embodiment the evaluating unit 208 may represent together with the input unit 301 and the display unit 302 an independent device which is combined with already existing hemodialysis apparatuses or hemofiltration apparatuses. It is merely necessary to ensure in this case that the corresponding tubing systems for the extracorporeal blood circuit comprise the temperature sensors 206 and 207 or that the temperature sensors 206 and 207 already connected to the evaluating unit 208 can be connected to the tubing systems. Furthermore, in this case on the control unit 106 a connection must be provided for the signal line 222 for entering the temperature desired value.

The invention has now been explained with reference to specific embodiments. Other embodiments will be apparent to those of ordinary skill in this art. It is therefore not intended that this invention be limited except as indicated by the appended claims.

I claim:

1. A method for withdrawing heat from blood in a extracorporeal circuit employing a treatment solution wherein blood is brought into contact with the treatment solution along a membrane and wherein the treatment solution has been heated in a source supplying the treatment solution, in order to maintain energy balance of a patient, the method comprising:
    establishing a reference temperature value for the blood prior to starting treatment;
    measuring the temperature of blood emerging from said patient's body during use of the treatment solution to obtain a first measured temperature value correlated with the body temperature of the patient;
    comparing the first measured temperature value with the reference value to obtain a comparison value; and
    continuously adjusting the temperature of the treatment solution in response to the comparison value to maintain the comparison value in order to maintain an energy balance of the patient.

2. The method according to claim 1 further including the step of performing hemodialysis with a dialysis solution, wherein said treatment solution is said dialysis solution.

3. The method according to claim 1 further including the step of performing hemofiltration with a substitution solution, wherein said treatment solution is said substitution solution.

4. The method according to claim 1 wherein said temperature measuring step comprises measuring arterial blood temperature.

5. The method according to claim 1 wherein said temperature measuring step comprises measuring venous blood temperature.

6. The method according to claim 1 wherein said reference value establishing step comprises:
    measuring arterial blood temperature prior to start of application of said treatment solution to the patient.

7. The method according to claim 6 further including the step of:
    integrating with respect to time the currently withdrawn energy to obtain total withdrawn energy for said time.

8. The method according to claim 1 wherein said reference value establishing step comprises:
    measuring the temperature difference between arterial blood temperature and venous blood temperature prior to start of application of said treatment solution to the patient to obtain a reference value representative of said reference temperature value.

9. The method according to claim 1 further including the steps of:
    measuring the arterial blood temperature;
    measuring the venous blood temperature;
    forming a current difference between the arterial blood temperature and the venous blood temperature;
    measuring volume of blood delivered in the extracorporeal circuit to obtain a withdrawn volume value; and
    calculating currently withdrawn energy from the current difference and the withdrawn volume value.

10. An apparatus for treating blood in an extracorporeal circuit comprising:
    a treatment element which is divided by a membrane into a first chamber and a second chamber,
    a treatment solution source, said first chamber being connected in a solution path with said treatment solution source,
    a temperature regulating unit, said treatment solution source being coupled to said temperature regulating unit,
    said temperature regulating unit having a temperature detector disposed within said treatment solution source, a heating means for heating solution in said treatment solution source and a first control unit,
    a conduit for conveying blood along a blood path,
    a blood pump, said blood pump being coupled in said blood path with said second chamber,
    a first temperature sensor disposed in said blood path upstream of said treatment element for measuring blood temperature emerging from the body of a patient, and
    a second control unit, said second control unit being coupled to said first temperature sensor and to said first control unit, said second control unit comprising a means for comparing an actual value received from said first temperature sensor with a preselected desired value and upon deviation therefrom regulating the temperature of said solution by controlling said first control unit to heat and cool said solution.

11. The apparatus according to claim 10 wherein said treatment element is a hemodialyzer or hemodiafilter and wherein said treatment solution is a dialysis solution.

12. The apparatus according to claim 10 further including a second temperature sensor coupled in said blood path downstream of said treatment element and coupled to said second control unit for providing temperature readings of blood returning to the body of the patient.

13. The apparatus according to claim 10 further including a programmable input device and wherein said second control unit is coupled to receive input control signals from said programmable input device.

14. The apparatus according to claim 10 wherein said second control unit is coupled to receive a predetermined temperature value and to receive blood flow information and further comprises means for determining amounts of energy withdrawn from the blood in order to determine amounts of energy to be returned to the blood by regulating the temperature of said solution by controlling said first control unit to heat and cool said solution.

15. The apparatus according to claim 10 further including means coupled to a display unit to receive temperature values and pump rates for displaying temperature values, pumping rates energy values.

16. An apparatus for treating blood in an extracorporeal circuit comprising:
a treatment element which is divided by a membrane into a first chamber and a second chamber,
a hemofiltrate receptacle, said first chamber being connected in a solution path with said hemofiltrate receptacle,
a conduit for conveying blood along a blood path,
a blood pump, said blood pump being coupled in said blood path upstream of said second chamber,
a substitution fluid supply unit coupled to said blood path through a supply conduit, said substitution fluid supply unit comprising a second pump for pumping a substitution fluid, a first control unit and a temperature regulating unit,
a first temperature sensor disposed in said blood path upstream of said treatment element for measuring blood temperature emerging from the body of a patient, and
a second control unit, said second control unit being coupled to said first temperature sensor and to said first control unit, said second control unit comprising a means for comparing an actual value received from said first temperature sensor with a preselected desired value and upon deviation therefrom regulating the temperature of said solution by controlling said first control unit to heat and cool said solution.

17. The apparatus according to claim 16 further including a second temperature sensor coupled in said blood path downstream of said treatment element and coupled to said second control unit for providing temperature readings of blood returning to the body of the patient.

18. The apparatus according to claim 16 further including a programmable input device and wherein said second control unit is coupled to receive input control signals from said programmable input device.

19. The apparatus according to claim 16 wherein said second control unit is coupled to receive a predetermined temperature value and to receive blood flow information and further comprises means for determining amounts of energy withdrawn from the blood in order to determine amounts of energy to be returned to the blood by regulating the temperature of said solution by controlling said first control unit to heat and cool said solution.

20. The apparatus according to claim 16 further including means coupled to a display unit to receive temperature values and pump rates for displaying temperature values, pumping rates energy values.

21. Device for determining heat flow of a blood cleaning apparatus having an extracorporeal blood circuit, said blood circuit being connected through a treatment element which is either a hemofilter or a dialyzing element, said blood circuit having a blood pump capable of pumping blood at a selected pump rate, said device comprising:
a first temperature sensor disposed in said blood circuit upstream of said treatment element;
a second temperature sensor disposed in said blood circuit downstream of said treatment element; and
a control unit, said control unit being coupled to said first temperature sensor, to said second temperature sensor and to said blood pump, said control unit comprising means for receiving as input signals a first temperature value from said first temperature sensor, a second temperature value from said second temperature sensor and a pump rate value of said blood pump, said control unit further comprising means for determining continuously from differences between said first and second temperature values and from said pump rate value said heat flow, and said control unit additionally comprising means for providing as an ongoing output said heat flow.

22. Device for determining heat flow of a blood cleaning apparatus having an extracorporeal blood circuit, said blood circuit being connected through a treatment element which is either a hemofilter or a dialyzing element, said blood circuit having a blood pump capable of pumping blood at a selected pump rate, said device comprising:
a temperature sensor disposed in said blood circuit upstream of said treatment element; and
a control unit, said control unit being coupled to said temperature sensor and to said blood pump, said control unit comprising means for receiving as input signals a first temperature value from said temperature sensor at the beginning of a treatment, a substantially continuous second temperature value from said temperature sensor during treatment and a pump rate value of said blood pump, said control unit further comprising means for determining continuously from differences between said first and second temperature values and from said pump rate value said heat flow, and said control unit additionally comprising means for providing as an ongoing output said heat flow.

* * * * *